United States Patent [19]

Baker

[11] 3,971,649
[45] July 27, 1976

[54] S-METHYL-N-[4-(4'-CHLOROPHENOXY)-PHENYL] THIOLCARBAMATE

[75] Inventor: Don R. Baker, Orinda, Calif.

[73] Assignee: Stauffer Chemical Company, Westport, Conn.

[22] Filed: July 23, 1975

[21] Appl. No.: 598,485

[52] U.S. Cl. .............................. 71/100; 260/455 A
[51] Int. Cl.² ................. C07C 155/02; A01N 9/12
[58] Field of Search ................. 260/455 A; 71/100

[56] References Cited
UNITED STATES PATENTS 3,632,631  1/1972  Wright ........................... 260/455 A

FOREIGN PATENTS OR APPLICATIONS 22,987  6/1974  Japan .............................. 260/455 A
4,534,808  11/1970  Japan .............................. 260/455 A OTHER PUBLICATIONS
J. Amer. Chem. Soc. vol. 77 pp. 581–583 (1954).

*Primary Examiner*—Lewis Gotts
*Assistant Examiner*—D. R. Phillips
*Attorney, Agent, or Firm*—Joel G. Ackerman

[57] ABSTRACT

The novel compound S-methyl-N-[4-(4'-chlorophenoxy)phenyl]thiolcarbamate,

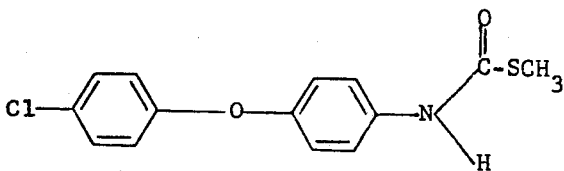

is useful as a post-emergence herbicide, particularly as a post-emergence, post-flooding herbicide for use in connection with rice cultivation.

3 Claims, No Drawings

S-METHYL-N-[4-(4'-CHLOROPHENOXY)PHENYL] THIOLCARBAMATE

PRIOR ART

Certain diphenyl ether ureas are known to be useful as herbicides. For example, U.S. Pat. No. 3,119,682 discloses certain mono- and dialkyl-amino diphenyl ether ureas as suitable herbicides.

SUMMARY OF THE INVENTION

This application relates to the novel compound S-methyl-N-[4-(4'-chlorophenoxy) phenyl] thiolcarbamate and its use as an herbicide. This compound has the formula:

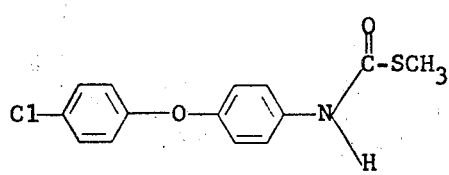

This compound has been found to be an active herbicide; that is, it has been found to be herbicidally effective against a variety of plant species. More particularly, it is characterized by having little or no pre-emergence herbicidal activity, but having primarily post-emergence herbicidal activity, primarily effecting broad-leaf vegetation. This compound has been found to have particular utility in rice cultivation in selectively affecting the growth of weeds or other undesirable vegetation while leaving rice plants substantially unaffected. The invention, therefore, also relates to a method of controlling undesirable vegatation comprising applying an herbicidally effective amount of the said compound to the area or plant locus where control is desired.

An herbicide as used herein means a compound which controls or modifies the growth of plants. By the term "herbicidally effective amount" is meant an amount of compound which causes a modifying effect upon the growth of plants. By "plants" is meant germinant seeds, emerging seedlings, and established vegetation, including the roots and above-ground portions. Such modifying effects include all deviations from natural development, for example, killing, retardation, defoliation, desiccation, regulation, stunting, tillering, stimulation, leaf burn, dwarfing, and the like.

The following is an example of preparation of the compound:

EXAMPLE

The following were mixed, in the order stated: 4.6 g (0.021 mole) 4-(4-chlorophenoxy)-aniline, 50 ml chloroform, 3 ml pyridine and 2.2 ml (0.025 mole) methyl chlorothiolformate. The reaction was isothermic on addition of the chlorothiolformate. The reaction mixture was let stand for 2 hours, then washed with 50 ml water, 25 ml 1N HCl, and a saturated $NaHCO_3$ solution, dried over $MgSO_4$ and evaporated in vacuo. The residue was washed with n-pentane. There resulted 5.7 g of S-methyl-N-[4-(4'-chlorophenoxy)phenyl]thiolcarbamate, m.p. 101°–103°C.

HERBICIDAL SCREENING TESTS

The S-methyl-N-[4-(4'-chlorophenoxy)phenyl]thiolcarbamate was tested as an herbicide in the following manner:

A. Pre-emergence Herbicide Screening Test: Using an analytical balance, 20 mg of the compound was weighed out on a piece of glassine weighing paper. The paper and compound were placed in a 30-ml wide-mouth bottle and 3 ml of acetone containing 1% Tween 20 added to dissolve the compound. The 3 ml of solution was sprayed uniformly on the soil contained in a small Styrofoam flat (7 inches long, 5 inches wide and 2.75 inches deep) one day after planting weed seeds in the flat or soil. A No. 152 DeVilbiss atomizer was used to apply the spray using compressed air at a pressure of 5 lb./sq. inch. The rate of application was 20 lb./acre.

On the day preceding treatment, the Styrofoam flat was filled to a depth of 2 inches with loamy sand soil. Seeds of seven different weed species were planted in individual rows using one species per row across the width of the flat. The seeds were covered with soil so that they were planted at a depth of 0.5 inch. The seeds used were hairy crabgrass (*Digitaria sanguinalis*), yellow foxtail (*Secaria glauca*), watergrass (*Enchinochloa crusgalli*), red oat (*Avena sativa*), redroot pigweed (*Amaranthus retroflexus*), Indian mustard (*Brassica juncea*), and curly dock (*Rumex crispus*). Ample seeds were planted to give about 20 to 50 seedling per row after emergence, depending on the size of the plants.

After treatment, the flat was placed in the greenhouse at a temperature of 70° to 85°F and watered by sprinkling. Two weeks after treatment, the degree of injury or control was determined by comparison with untreated check plants of the same age. The injury rating from 0 to 100% was recorded for each species as percent control with 0% representing no injury and 100% representing complete kill.

B. Post-emergence Herbicide Screening Test: Seeds of six plant species, including hairy crabgrass, watergrass, red oat, mustard, curly dock and pinto beans (*Phaseolus vulgaris*) were planted in a Styrofoam flat as described above for pre-emergence screening. The flat was placed in the greenhouse at 70° to 85°F and watered daily with a sprinkler. About 10 to 14 days after planting when the primary leaves of the bean plants are almost fully expanded and the first trifoliate leaves are just starting to form, the plants were sprayed. The spray was prepared by weighing out 20 mg of the compound, dissolving it in 5 ml of acetone containing 1% Tween 20 and then adding 5 ml of water. The solution was sprayed on the foliage using a No. 152 DeVilbiss atomizer at an air pressure of 5 lb./sq. inch. The spray concentration was 0.2% and the rate was 20 lb./acre. Injury ratings were determined as above.

C. Postflood — Postemergence Application to Paddy Rice: A plastice tub, 10 × 7.5 × 5.75 inches was filled to a depth of 2 inches with 8 pounds of a loamy sand soil pretreated with 50 ppm Captan × 50W and 18. 18. 18 fertilizer. One pint of the soil was removed, the remaining soil was leveled and seven rows were impressed across the width of the flat. Three dayflower (*Commelina diffusa*) cuttings 3 to 4 inches long, six yellow nutsedge tubers (*Cyperus esculentus*), and seeds of annual morningglory (*Ipomoea purpurea*), curly dock (*Rumex crispus*), sesbania (*Sesbania spp.*) and rice (*Oryza sativa*) were planted in separate rows. The pint of soil was used to cover 0.5 inches deep the seeds, tubers and part of the cuttings. The planted soil was placed in a greenhouse, and irrigated by sprinkling as needed to keep the soil moist. Three days after the initial seeding another row was impressed 0.5 inches deep across the width of the flat and seeds of watergrass (*Echinochloa crusgalli*) were planted and covered by pinching together the soil on either side of the seeder row. Seven to ten days after the original seeding, the soil was flooded with 2 inches of water. At flooding time the grass species were in the two-leaf stage 1 to 2 inches high, the nutsedge was 1 inch high, the curly dock was in the cotyledon stage about 1 inch high, the other broadleaf species were 2 to 3 inches high and the dayflower was rooted with little new growth. The compound was applied by pipetting into the flood water a stock solution of the compound dissolved in 20 ml of acetone containing 1% Tween 20 at a level proportionate to 2 lb./acre of the test compound. The water level in the tub was maintained by adding water as needed. Three weeks after application the species were rated visually as percent control from 0 to 100%, where 0% represents no injury and 100% represents complete kill when compared to the untreated check. The rice was substantially unaffected. The percent control was based on the total injury to the other plants.

The results of these tests are given in the following table. The values given for the compound related to percent control for seven plant species tested pre-emergence and six plant species tested post-emergence. A value of 21 indicated 70 to 100% control for pre-emergence; a value of 18 indicated 70 to 100% control for post-emergence. The post-flood, post-emergence rice result is given with respect to 100% control.

| | Herbicide Test Results | |
|---|---|---|
| Pre-Emergence | Post-Emergence | Post-Flood |
| 4 | 16 | 52 |

In practice, the compound is formulated with an inert carrier, utilizing methods well-known to those skilled in the art, thereby making it suitable for application as dusts, sprays, or drenches and the like, in the form and manner required. The mixtures can be dispersed in water with the aid of a wetting agent or they can be employed in organic liquid compositions, oil and water, water in oil emulsions, with or without the addition of wetting, dispersing or emulsifying agents. An herbicidally effective amount depends upon the nature of the seeds or plants to be controlled and the rate of application varies from 0.5 to approximately 50 pounds per acre.

Compositions utilizing the compound of the present invention are most advantageously applied in the post-emergence, post-flood stage, for example by spraying from either aircraft or with hand-held or other ground-level sprayers. Incorporation of the compound into the flood water is most advantageously performed when the rice is at a height of several inches above the water; if applied too early the compound could cause injury to the very young rice plants, if applied much later the compound would not be as effective against fully-grown weed species.

What is claimed is:

1. A compound having the formula

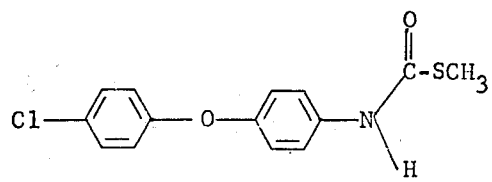

2. A method of controlling undesirable vegetation comprising applying to the locus thereof an herbicidally effective amount of a compound having the formula

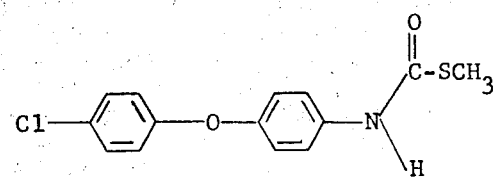

3. An herbicidal composition of matter comprising an herbicidally effective amount of a compound having the formula

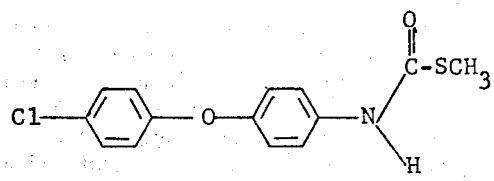

and and inert carrier.

* * * * *